(12) United States Patent
Geisser et al.

(10) Patent No.: US 9,193,651 B2
(45) Date of Patent: Nov. 24, 2015

(54) PROCESS FOR THE CHEMOSELECTIVE REDUCTION OF TERMINALLY SATURATED CARBOXYLIC ESTERS

(71) Applicant: Givaudan, S.A., Vernier (CH)

(72) Inventors: Roger Wilhelm Geisser, Zürich (CH); Andreas Goeke, Winterthur (CH); Fridtjof Schroeder, Hettlingen (CH)

(73) Assignee: Givaudan S.A., Vernier (CH)

( * ) Notice: Subject to any disclaimer, the term of this patent is extended or adjusted under 35 U.S.C. 154(b) by 0 days.

(21) Appl. No.: 14/398,076

(22) PCT Filed: May 16, 2013

(86) PCT No.: PCT/EP2013/060150
§ 371 (c)(1),
(2) Date: Oct. 30, 2014

(87) PCT Pub. No.: WO2013/171302
PCT Pub. Date: Nov. 21, 2013

(65) Prior Publication Data
US 2015/0152029 A1    Jun. 4, 2015

(30) Foreign Application Priority Data
May 16, 2012 (GB) .................... 1208589.0

(51) Int. Cl.
*C07C 29/149* (2006.01)
*C07C 67/08* (2006.01)

(52) U.S. Cl.
CPC .................... *C07C 29/149* (2013.01)

(58) Field of Classification Search
CPC .............................. C07C 29/149; C07C 67/08
USPC .......................................................... 568/885
See application file for complete search history.

(56) References Cited

U.S. PATENT DOCUMENTS

| 2010/0130754 A1 | 5/2010 | Saudan et al. |
| 2014/0328748 A1 | 11/2014 | Goussev et al. |

FOREIGN PATENT DOCUMENTS

| WO | WO 2006/106483 A1 | 10/2006 |
| WO | WO 2006/106484 A1 | 10/2006 |
| WO | WO 2013/023307 A1 | 2/2013 |

OTHER PUBLICATIONS

PCT/EP2013/060150—International Search Report, mailed Aug. 29, 2013.
PCT/EP2013/060150—International Written Opinion, mailed Aug. 29, 2013.
PCT/EP2013/060150—International Preliminary Report on Patentability, issued Nov. 18, 2014.
GB 1208589.0—Great Britain Search Report, Sep. 17, 2012.
Saudan, et al., "Dihydrogen Reduction of Carboxylic Esters to Alcohols Under the Catalysis of Homogeneous Ruthenium Complexes: High Efficiency and Unprecedented Chemoselectivity", Angewandte Chemie International Edition, Aug. 14, 2007, pp. 7473-7476, vol. 46.

*Primary Examiner* — Sikarl Witherspoon
(74) *Attorney, Agent, or Firm* — Curatolo Sidoti Co., LPA; Joseph G. Curatolo; Salvatore A. Sidoti

(57) ABSTRACT

The chemoselective reduction of a carboxylic ester (I) to an alcohol by catalytic hydrogenation, in particular in the presence of a transition metal complex, more particularly in the presence of a ruthenium (II) complex is described.

20 Claims, No Drawings

PROCESS FOR THE CHEMOSELECTIVE REDUCTION OF TERMINALLY SATURATED CARBOXYLIC ESTERS

CROSS REFERENCE TO RELATED APPLICATIONS

This application is a national stage application of International Application No. PCT/EP2013/060150, filed 16 May 2013, which claims priority from Great Britain Patent Application No. 1208589.0, filed 16 May 2012, from which applications priority is claimed, and which are incorporated herein by reference.

The present invention relates to fragrance ingredients and methods of forming same.

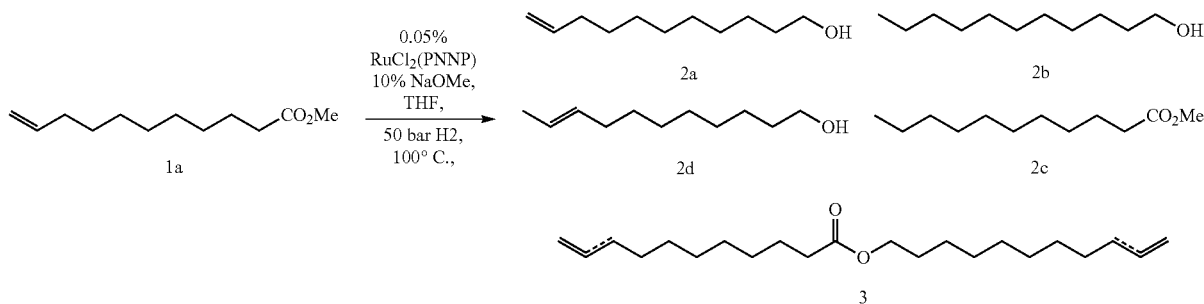

There are many interesting fragrance molecules containing alcohol functionality. Rosalva™ (9-decenol) is an example of such an interesting fragrance ingredient, which is highly desirable for its floral-rosy-fatty aldehydic smell. The chemistry into such interesting fragrant alcohols might involve the catalytic hydrogenation of a corresponding ester to produce the alcohol.

Synthetic procedures and reagents for reducing esters to alcohols are known in the art. WO2006106483 discloses a class of bidentate ruthenium (II) complexes that are useful in the catalytic hydrogenation of esters and WO 2013023307 discloses a class of tridentate complexes for this purpose. Similarly, WO2006106484 discloses a class of tetradentate ruthenium complexes that are useful in the catalytic hydrogenation of esters.

Rosalva™ represents an interesting synthetic challenge, however, in that the corresponding ester (e.g. methyl or ethyl decenoate) contains a carbon-carbon double bond that would be susceptible to competitive hydrogenation. Indeed, owing to its position on the terminus of the carbon chain, this double bond might be considered to be particularly labile.

Saudan et al in Angew. Chem. Int. Ed. 2007 46 7473-7476 discuss the reduction of carboxylic esters to alcohols using ruthenium complexes, and in particular the ruthenium complexes disclosed in the aforementioned WO2006106483 and WO2006106484. The authors discuss the chemoselectivity of the hydrogenation reaction with reference to certain substrates containing both an ester double bond and a carbon-carbon double bond. Although they do describe reactions that are highly chemoselective for ester reduction, when 10-undecenoate 1a is employed as a substrate (having an aliphatic terminal carbon-carbon double bond), after 2.5 hours the reaction is not at all chemoselective for the ester group, but gives saturated alcohol product 2b, which has been reduced at the carbon-carbon double bond as well as the ester functionality.

However, when the same reaction is stopped after only 23 minutes, only 75% of substrate 1a is converted giving 47% unsaturated alcohol 2a, 5% saturated alcohol 2b, 3% saturated ester 2c and 20% of transesterification products 3. The mentioning of (multiple) "transesterification products" (3) indicates that double bond isomers were detected. This in turn indicates that unsaturated alcohol 2a also contains double bond isomers, e.g. 9-undecenol 2d. The chemoselectivity of the reduction for the ester double bond compared to the one of the carbon-carbon double bond (CO/DB selectivity) is 85:15 if one combines the undesired products reduced at the terminal double bond (2b and 2c). If one takes into account that 2a probably contains isomers such as 2d the chemoselectivity towards 2a should be even lower. Based on their findings, the authors conclude that the reaction could be optimised to selectively reduce ester 1a to 2a.

This conclusion is curious. Analysing the content of the reaction mixture at only a single point in time and at such an early period of time when there is only slightly more than 50% conversion of ester groups, can hardly be considered predictive of the course of a reaction, and certainly says nothing about the relative amounts of unsaturated and saturated alcohol that will be present in the reaction mixture once the reaction has proceeded with full, or substantially full, conversion of the ester. Finally, the authors offer no explanation or guidance regarding how this reaction might be optimised to provide a chemoselective process that proceeds with very high conversion of the carboxylic ester.

For a process to be useful in an industrial context it must achieve the required high chemoselectivity but it must also proceed with full, or substantially full, conversion of the carboxylic ester.

There is a need for an industrially acceptable process of preparing alcohols with a terminal double bond from substrates containing both ester and terminal carbon-carbon bonds, which proceeds with high conversion, e.g. >80%, more particularly >85%, more particularly >90%, more particularly >95%, and still more particularly 99-100%, and with high chemoselectivity for the ester double bond. By "high chemoselectivity" is meant that, the ratio of unsaturated alcohol to saturated alcohol produced in a reaction may be 6:1 or greater, more particularly 7:1 or greater, still more particularly 8:1 or greater, still more particularly 9.1, still more particularly 10:1 or greater The invention addresses the problems with the prior art and provides in a first aspect a process for the chemoselective reduction of a terminally unsaturated carboxylic ester (I) to a terminally unsaturated alcohol (II) by catalytic hydrogenation, in particular, in the presence of a transition metal complex, more particularly a ruthenium (II) complex

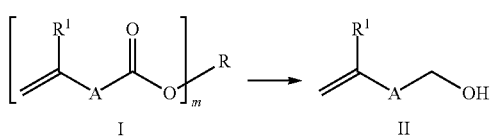

wherein A is a divalent radical containing 1 to 30 carbon atoms, which may be linear or branched, substituted or unsubstituted aliphatic, aromatic or contain both aliphatic and aromatic elements; R is a hydrocarbon radical or a radical derived from a hydrocarbon, which may be substituted or unsubstituted and saturated or unsaturated; $R_1$ is a hydrogen atom or a $C_{1-20}$ linear or branched, substituted or unsubstituted alkyl or alkene group; and m is an integer from 1 to 6.

When the radical A, is an aromatic radical, or contains aromatic elements, it may contain one or a multiple of aromatic rings, and any aromatic rings may contain heteroatoms, including N, O or S-atoms.

In an embodiment of the present invention the radical R is selected from a linear or branched, saturated or unsaturated, substituted or unsubstituted $C_{1-20}$ hydrocarbon group. When R is substituted, the substituent may be selected from any of those substituents referred to hereinabove. In a more particular embodiment the radical R is methyl, ethyl, linear or branched propyl or linear or branched butyl. More particularly, the radical R is ethyl.

In a particular embodiment the invention provides a process for the chemoselective reduction of a terminally unsaturated carboxylic ester to a terminally unsaturated alcohol by catalytic hydrogenation, in particular, in the presence of a transition metal complex, more particularly a ruthenium (II) complex

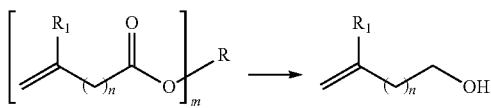

wherein R, $R_1$ and m are as herein defined, and wherein n is an integer from 1 to 10.

Still more particularly, R is methyl or ethyl, m is 1. More particularly still, R is methyl or ethyl, m is 1, and n is 7 or 8.

Still more particularly, the carboxylic ester is methyl 9-decenoate, ethyl 9-decenoate, methyl 10-undecenoate or ethyl 10-undecenoate.

More particularly still, the carboxylic ester is ethyl 9-decenoate or ethyl 10-undecenoate.

In another embodiment the radical R may be a di-, tri- or multi-valent hydrocarbon radical or radical derived from a hydrocarbon. In particular, the radical R may be such that the ester of formula Ia is represented by the formula

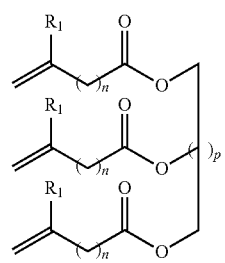

wherein p is zero or an integer from 1 to 4 and n and $R_1$ are as hereinabove defined. More particularly, p is zero or 1. Still more particularly, p is zero or 1 and n is 7 or 8.

A characteristic of all the carboxylic esters I that can serve as starting substrates in a process according to the invention is that they contain a carbon-carbon double bond at the terminus of a chain. Mono-or di-substituted alkene groups such as these are believed to be particularly labile and therefore more susceptible to compete with the ester double bond during hydrogenation.

In a particular embodiment of the present invention, the process proceeds in the presence of a homogeneous ruthenium (II) complex.

The ruthenium complex employed in the present invention may be any of those complexes disclosed in WO2006106484, which document, for the purpose of disclosing the ruthenium complexes contained therein, is hereby incorporated by reference.

In a particular embodiment of the present invention, the ruthenium(II) complex is a complex with a tetradentate ligand wherein the coordinating groups of said ligand consist of at least one imino or amino group and at least one phosphino group. Examples of suitable catalysts are described in WO2006106484.

More particularly still, the ruthenium complex is represented by the formula 4a or 4b

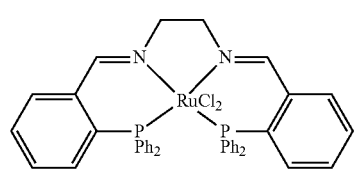

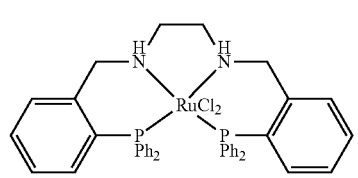

whose syntheses has been reported by Gao et al. in Polyhedron 15, 1241, 1996.

It has now been found that the unsaturated carboxylic esters referred to hereinabove can be converted completely or nearly completely to their alkenols II, with a significantly improved chemoselectivity towards ester hydrogenation. An improved chemoselectivity in ester hydrogenation means that side reactions such as alkene hydrogenation and/or alkene isomerization are substantially suppressed.

As stated hereinabove, the reaction proceeds with high chemoselectivity with complete or substantially complete conversion of the ester functionality, e.g. >80%, more particularly >85%, more particularly >90%, more particularly >95%, and still more particularly 99-100%, of the ester functionality is converted.

The substrate (starting material)/catalyst ratio can influence the chemoselectivity and conversion of the reaction of present invention. In a particular embodiment of the present invention the substrate/catalyst ratio is greater than 2000, more particularly greater than 10000, still more particularly greater than 20000, wherein the ratio is a molar ratio.

More particularly, the applicant found that the amount of ruthenium (II) complex employed can affect the extent of conversion of the carboxylic esters, as well as the chemoselectivity of the reaction such that high levels of the complex tend to promote a fast and complete conversion of the terminally unsaturated carboxylic ester, but chemoselectivity may be compromised. Conversely, with low levels one observes low and incomplete conversion, but chemoselectivity will be higher. Surprisingly however, the applicant has found that conversion levels referred to hereinabove, and more particularly of 90% or higher, e.g. 90 to 100% can be obtained, whilst at the same time the reaction proceeded with high chemoselectivity, that is, the ratio of unsaturated alcohol to saturated alcohol was 6:1 or greater, more particularly 7:1 or greater, still more particularly 8:1 or greater, still more particularly 9.1, still more particularly 10:1 or greater, in particular if the ruthenium (II) complexes are employed in amounts of less than 0.05 mol %, more particularly 0.01 mol % or less, still more particularly 0.005 mol % or less. An illustrative range of concentrations for the ruthenium (II) complex useful in the present invention is 0.04 to 0.001 mol % relative to the amount of substrate.

Still further, low catalyst levels are important because this efficiently reduces the overall costs of catalytic homogeneous hydrogenation reactions.

In a particular embodiment of the present invention, substrate (I) is either an ethyl ester or a higher ester, for example n-propyl, iso-propyl, n-butyl, tert-butyl, iso-butyl or even higher branched and unbranched esters.

The applicant found that, in contrast to terminally unsaturated methyl alkenoates, ethyl, propyl or higher alkenoates caused an unexpected rate acceleration. As such, lower catalyst loadings could be employed when using ethyl and higher esters, and this in turn provided much higher selectivities for the reduction of the ester functionality.

The rate acceleration in case of terminally unsaturated ethyl or higher alkyl ester substrates was unexpected and surprisingly high. Whereas, it has been observed by Saudan et al in Angew. Chem. Int. Ed. 2007, 46, 7473-7476 that branched (isopropyl) or higher (benzyl) alkyl benzoates were more efficiently reduced than methyl benzoate, the benzoates are, in contrast to alkanoates or alkenoates with a $CH_2$-group in their α-position, activated esters whose activity in ester reduction reactions is not comparable to the ones of alkanoates, which lack a positive neighbour-group effect.

Metal alkanoates are preferred bases for use in the present invention. The metals may be Na, K or Cs; whereas the alkanoates may be $C_1$ to $C_{10}$ alkanoates, which may be linear or branched.

The metal alkanolate may be used in any amounts between 1 mol-equivalent per substrate and 1 mol-equivalent per catalyst, but typically in amounts of 5-15% per substrate to obtain reproducible results and to keep the cost contribution of the base low.

The solvent employed in the base/solvent system can be any solvent that is typically employed in homogeneous catalytic hydrogenation reactions. Non-limiting examples of solvents include aromatic solvents such as toluene or xylenes; hydrocarbon solvents such as hexane or cyclohexane; ethers such as tetrahydrofuran or MTBE; and polar solvents such as tert-butanol. Methanol should be avoided. Preferred solvents are ethers or furanes such as THF or analogues such as cyclopentyl methyl ether (CPME), methyltetrahydrofurane, but any acyclic or cyclic polyethers such as dioxane or tetraethyleneglykoldiethyl ether can be also used.

More particularly, the reaction proceeds with high chemoselectivity and with complete or substantially complete conversion of the ester functionality if low levels of solvent, or even solvent-free systems are employed. Low levels of solvent include <100% solvent per substrate in weight equivalents (w/w), <50% w/w, <25% w/w or preferable <10% w/w.

When solvent is employed, its use can be limited to an amount just sufficient for catalyst dissolution/emulsification and for subsequent transfer and addition of the thus-prepared catalyst solution to the substrate. Apart from these negligible solvent-quantities the reaction can be carried out essentially solvent-free.

Under strict solvent-free conditions the catalyst is dissolved in a fraction of the substrate before this fraction is added to the remaining substrate or vice versa.

Particularly efficient base/solvent systems include KOMe in THF or NaOMe in toluene. These two base/solvent systems are preferred over the system NaOMe/THF used by Saudan et al (vide supra) for the CO-selective reduction of methyl undecenoate 1a. The applicant has found that certain base/solvent systems such as NaOMe in toluene or KOMe in THF greatly enhance turnover number (TON) and turnover frequency (TOF) when compared with prior art base/solvent systems. The TON is directly related to substrate/catalyst ratios at a given conversion, whereas the TOF is the TON per unit time as is more fully described in Jens Hagen, Industrial Catalysis: A Practical Approach, Weinheim, Germany: Wiley-VCH 2005.

In a particular embodiment of the present invention a sacrificial terminal alkene may be employed in the reaction mixture.

Although the substrate/catalyst ratio, the nature of the ester substituent R, and the nature of the base/solvent system can positively influence the efficiency and the ester-selective catalytic homogeneous hydrogenation of terminally unsaturated esters such as I and II, it is nevertheless desirable to avoid hydrogenation of the terminal double bond after the ester function has been reduced.

One can adjust reaction conditions (e.g. pressure, temperature) to influence this, but applicant has found that the use of sacrificial terminal alkenes, for example terminal alkene III is beneficial in this regard.

III

These alkenes (III) are chosen from the group of terminal monosubstituted alkenes (R'=H) or 1,1-disubstituted methylene compounds (R and R'≠H). R and R" can be H, or optionally substituted alkyl, alkenyl, or aryl. R' and R" can be bound together to form a ring system or ring systems. The ring system or systems can be optionally substituted. When the groups representing R' or R" are substituted, the substituent can contain any of the main group elements such as O, S or N. More specifically the terminal alkene (III) is chosen from any terminal $C_6$-$C_{30}$ alkene, diene, triene or polyene, all of which may be substituted or unsubstituted. The unsaturation can be conjugated such as in isoprene, myrcene, farnesene, or part of an aromatic system as in styrene, all optionally substituted.

When employed, the sacrificial alkene may be added in amounts of 0.1-10 mol-equiv, ideally in amounts of 0.2-3 mol equiv. The molecular weight of the sacrificial alkene is chosen as such that it can be easily separated from the hydrogenation product by distillation.

Monosubstituted alkene or 1,1'-disubstituted methylene additives (III) can be chosen from any terpene compound, such as limonene, or can be in conjugation with other double bonds, such as in isoprene or myrcene, or can be in conjugation with aromatic systems (such as in α-methylstyrene).

In a particular embodiment of the invention, the sacrificial alkene III used in this invention is selected such that it is a low viscosity liquid. As such, it can act as a solvent and can be used to dissolve and aid the addition of catalyst to the substrate without using any other solvent. With the sacrificial alkene acting in this fashion, the hydrogenation can be carried out therefore under essentially solvent-free conditions and under industrial conditions which allow addition of the catalyst in a solvent.

It is also possible to use the ester intermediate IIIa as a sacrificial alkene. This intermediate is formed and accumulated during the process of the present invention by transesterification of substrate I with reduced alkenol product II and undergoes reduction, in case of lower reactivity of IIIa compared to I, when I has been completely consumed.

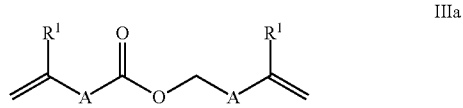

IIIa

Because isomerization/hydrogenation of the terminal double bonds of II and III take place at the end of the reaction it is preferable to stop the reaction when I has been completely consumed and only about 1-10% of IIIa are left and II has not yet suffered from hydrogenation and/or isomerization. After work-up II is easily separated from IIIa by distillation due to their very different molecular weights.

In a particular embodiment of the present invention the process of the present invention proceeds by employing a substrate/catalyst ratio greater than 2000; and/or employing an ester substrate (I) which is an ethyl ester or higher ester as defined herein above; and/or employing an efficient base/solvent system such as NaOMe/toluene or KOMe/THF; and or employing a sacrificial alkene as hereinabove defined.

The transition metal complexes employed for this reaction, e.g. the ruthenium (II) complexes 4a or 4b may not itself be catalysts in the homogeneous catalytic reduction of carboxylic esters with hydrogen. Active catalyst species 4c or 4d may be generated in situ with a base and can consist of $RuX_2$ cores with X=H and/or halides. It is also understood that complexes 4c or 4d can be independently synthesized and used under moisture and air-free conditions and can be used for the catalytic hydrogenation of substrates such as I. In case of $RuX_2=RuH_2$ no base or much reduced amounts of base may be necessary.

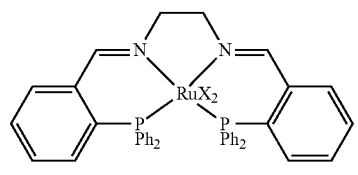

4c

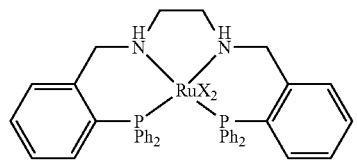

4d

Furthermore any carbon of the ligand of catalysts 4 can be optionally substituted.

The reaction may be carried out in an autoclave at a $H_2$ pressure ranging from 1 to 80 bars, or even higher, more particularly 40 to 80 bar or higher. The skilled person will understand that the $H_2$ pressure may be adjusted to optimise for the level of complex used.

The temperature at which the reaction may be carried out may vary depending on such factors as the melting/boiling point, the viscosity and the polarity of the substrate employed and the reaction products as well as the desired reaction time to achieve full, or substantially full conversion. Typically, however, the reaction will be carried out between 50 and 120 degrees centigrade.

There now follows a series of examples that further act to illustrate the invention.

General Conditions:

Non-commercial ester substrates were purified by flash chromatography and/or distillation before use.

Non-polar GCMS: 50° C./2 min, 20° C./min 200° C., 35° C./min 270° C. GCMS Agilent 5975C MSD with HP 7890A Series GC system. Non-polar column: BPX5 from SGE, 5% phenyl 95% dimethylpolysiloxan 0.22 mm×0.25 mm×12 m. Carrier Gas: Helium. Injector temperature: 230° C. Split 1:50. Flow: 1.0 ml/min. Transfer line: 250° C. MS-quadrupol: 106° C. MS-source: 230° C.

EXAMPLE 1

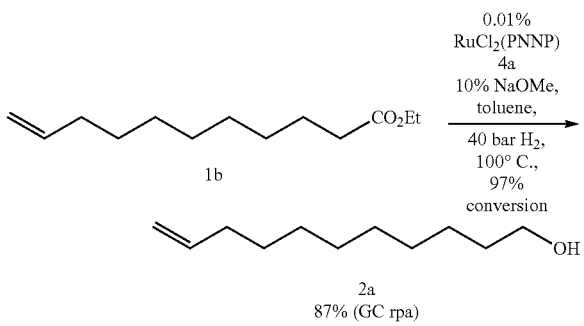

Under argon, toluene (3 ml) is added to a glass vial (50 ml) containing $RuCl_2$(PNNP) catalyst 4a (2.5 mg, 0.01 mol %) and NaOMe (0.163 g, 3 mmol). The suspension is treated in an ultrasonic bath until a reddish solution is obtained (3-5 min) to which a solution of ethyl 10-undecenoate (6.4 g, 29 mmol) in toluene (18 ml) is added. The vial is capped (crimp cap & silicone septum), punctured with a needle and put in a Parr autoclave. While stirring with a magnetic stirrer the autoclave is flushed three times with hydrogen, then put under hydrogen pressure (40 bar) and heated to 100° C. After 4 hours the heating is stopped and the pressure released. To the colourless reaction mixture is added 2% $H_3PO_4$ (4 ml) and diethyl ether (10 ml). The organic phase is washed with brine, dried over $MgSO_4$ and concentrated in vacuo. GC-MS analysis revealed 3% substrate 1b, 87% 10-undecenol 2a, 9% undecanol 2b, and 1% transesterification product 3. CO/DB selectivity: 91:9.

The analytical data of ethyl undec-10-enoate 1b, 10-undecenol 2a and undecanol 2b were identical with the ones from commercial samples of these compounds.

EXAMPLE 2

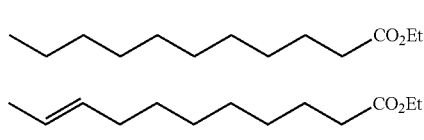

The reaction was carried out as described in Example 1 but in THF (instead of toluene) under 30 bar of hydrogen. After 4 h a very incomplete conversion (16%) to the undesired by-products 1c (8%) and 1d (8%) was detected.

The analytical data of ethyl undecanoate 1c were identical with the ones from the literature.

The analytical data of ethyl undec-9-enoate 1d are partially known from the literature (*J. Org. Chem.* 27, 3722, 1962). MS of 1d: 212 (3%, M+), 167 (11%), 166 (20%), 149 (10%), 137 (12%), 124 (38%), 123 (20%), 101 (32%), 88 (42%), 69 (40%), 55 (100%), 41 (51%), 29 (27%).

EXAMPLE 3

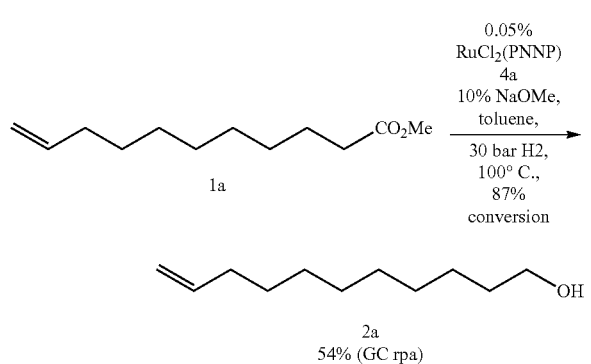

The reaction was carried out as described in Example 1 but with methyl undecenoate 1a and 0.05% RuCl$_2$(PNNP) catalyst 4a. After 3 h a 87% conversion to 10-undecenol 2a (54%), 9-undecenol 2d (8%), undecanol 2b (15%), methyl undecanoate 2c (3%) and transesterification products 3 (7%) was detected by GC. The CO/terminal double bond (DB) selectivity was 68:32

The analytical data of 10-undecenol 2a, undecanol 2b and methyl undecanoate 2c are identical with the ones obtained from commercial samples of these compounds. The analytical data of 9-undecenol 2d (partially in *J. Organomet. Chem.* 691, 5278, 2006 and references) and undecenoic acid undecenyl ester 3 (*Tetrahedron* 63, 11325, 2007) were identical with the ones described in the literature. MS of 2d: 152 (5%, [M-18]+), 124 (7%), 123 (8%), 110 (11%), 109 (14%), 96 (29%), 95 (30%), 82 (44%), 81 (49%), 68 (49%), 67 (54%), 55 (100%), 54 (36%), 41 (43%).

EXAMPLE 4

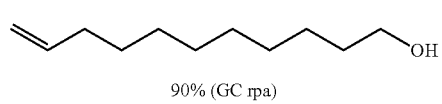

90% (GC rpa)

Under argon, RuCl$_2$(PNNP) catalyst 4a (7.5 mg, 0.01 mol %) in toluene (5 ml) are treated 5 min with ultrasound to give a fine suspension which is added to a suspension of ethyl 10-undecenoate 1b (19.2 g, 90 mmol) and NaOMe (0.5 g, 9 mmol) in toluene (16 ml) in a 120 ml Premex autoclave under argon. The autoclave is flushed three times with hydrogen and then heated at 100° C. under 50 bar hydrogen and 1200 rpm with overhead stirring. After 6 hours the GC-analysis revealed 6% substrate 1b, 90% 10-undecenol 2a, 4% undecanol 2b. CO/DB selectivity: 96:4. After 20 h the autoclave is cooled, the pressure released and the content of the autoclave poured onto 2% H3PO4 (10 ml). After phase separation the organic phase is washed with water (2×30 ml), dried over MgSO4, filtered and evaporated. The residue of 15.6 g consisted of 80% 10-undecenol 2a, 15% undecanol 2b and 5% isomer 2d according to GCMS and NMR.

EXAMPLE 5

Under argon, RuCl$_2$(PNNP) catalyst 4a (3.7 mg, 50 ppm) in distilled and degassed THF (5 ml) is treated for 5 min with ultrasound to give a fine suspension which is added to a suspension of KOMe_(0.63 g, 9 mmol) in ethyl 10-undecenoate 1b (19.2 g, 90 mmol) and distilled and degassed THF (58 ml) in a 120 ml Premex autoclave under argon. The autoclave is flushed three times with hydrogen and then heated at 100° C. under 50 bar hydrogen and 1200 rpm with overhead stirring. After 5 hours the heating is stopped, the pressure released and the content of the autoclave poured onto 2% H$_3$PO$_4$ (10 ml). After phase separation the organic phase is washed with water (2×30 ml), dried over MgSO$_4$, filtered and evaporated. GC-analysis of the quantitatively obtained material revealed 94% 10-undecenol 2a and 6% undecanol 2b.

EXAMPLE 6

Under argon, RuCl$_2$(PNNP) catalyst 4a (3.7 mg, 50 ppm) in distilled and degassed THF (5 ml) is treated for 5 min with ultrasound to give a fine suspension, which is added to a suspension of KOMe (0.63 g, 9 mmol) in ethyl 10-undecenoate 1b (19.2 g, 90 mmol) without additional solvent in a 120 ml Premex autoclave under argon. The autoclave is flushed three times with hydrogen and then heated at 100° C. under 50 bar hydrogen and 1200 rpm with overhead stirring. After 4 hours the heating is stopped and the pressure released. GC-analysis revealed 92% 10-undecenol 2a and 8% undecanol 2b.

EXAMPLE 7

The reaction is carried out as described in Example 6 but with RuCl$_2$(PNHNHP) catalyst 4b. After 2 hours GC-analysis revealed 4% substrate 1a, 90% 10-undecenol 2a, 6% undecanol 2b and 1% methyl undec-10-enoate 1a. CO/DB selectivity: 94:6.

EXAMPLE 8

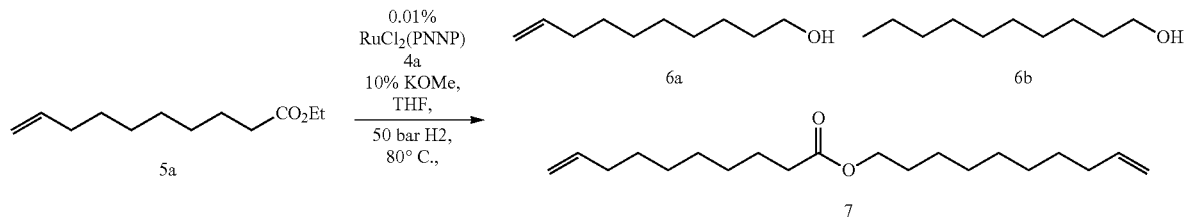 [SMILES: C=CCCCCCCCCO ; CCCCCCCCCCO ; C=CCCCCCCCC(=O)OCC ; C=CCCCCCCCCOC(=O)CCCCCCCC=C]

Under argon, RuCl$_2$(PNNP) catalyst 4a (7.6 mg, 0.01%) in distilled and degassed THF (5 ml) is treated for 5 min with ultrasound to give a fine suspension, which is added to a suspension of KOMe (0.63 g, 9 mmol) in ethyl 9-decenoate 5a (18 g, 91 mmol) (P. Evans, M. Leffray, *Tetrahedron* 59, 7973-7981, 2003) in a 120 ml Premex autoclave under argon. The autoclave is flushed three times with hydrogen and then heated at 80° C. under 50 bar hydrogen and 1200 rpm with overhead stirring. After 3 hours GC-analysis revealed 86% dec-9-enol 6a, 10% decanol 6b and 3% of intermediate 7. CO/DB selectivity: 90:10.

The analytical data of dec-9-enol 6a and decanol 6b were identical with the ones obtained from commercial samples, e.g. Rosalva™. The analytical data of 9-decenyl 9-decenoate 7 were identical with the ones known from the literature e.g. S. S. Narine et al., *Ind. Eng. Chem. Res.* 52, 2740, 2013. MS of 7: 171 (1%), 153 (3%), 152 (4%), 139 (6%), 135 (8%), 123 (5%), 110 (16%), 109 (15%), 97 (20%), 96 (29%), 95 (16%), 84 (12%), 83 (34%), 82 (30%), 81 (22%), 69 (36%), 68 (28%), 67 (29%), 55 (100%), 54 (26%), 43 (16%), 41 (46%).

EXAMPLE 9

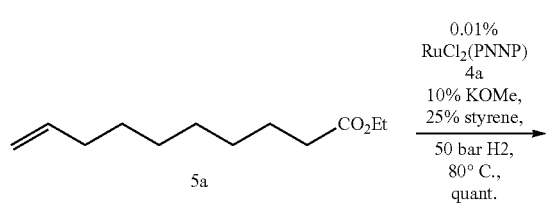

-continued

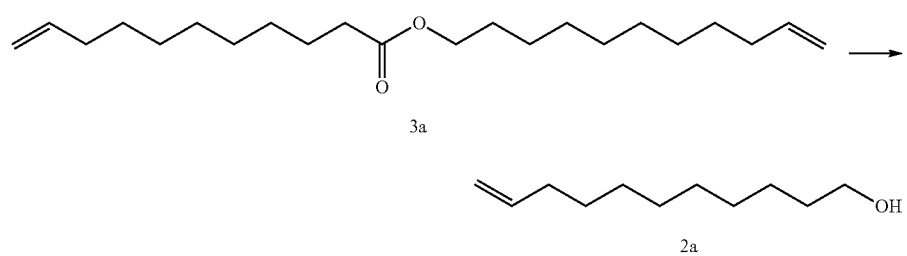

Under argon, RuCl$_2$(PNNP) catalyst 4a (21 mg, 0.01%) in styrene (12.75 g, 0.12mol) is treated for 5 min with ultrasound to give a fine suspension which is added to a suspension of KOMe (1.8 g, 25 mmol) in ethyl 9-decenoate 5a (50 g, 0.25 mol) in a 120 ml Premex autoclave under Argon. The autoclave is flushed three times with hydrogen and then heated at 80° C. under 50 bar hydrogen and 1200 rpm with overhead stirring. The progress of the reaction was monitored by GC. After 5 hours (96% dec-9-enol 6a and 4% decanol 6b according to GC) the heating is stopped and the pressure released. After addition of 2% H$_3$PO$_4$ (30 ml) the organic phase is washed with water (2×50 ml), dried over MgSO$_4$, filtered and concentrated under reduced pressure. The crude product (41 g) is treated with paraffin oil (4 g) and K$_2$CO$_3$ (0.3 g) and is distilled at 0.02 mbar to give 33.2 g (84%) of product (96% dec-9-enol 6a and 4% decanol 6b) as colourless oil at 65° C. Residues: 4.6 g.

Reaction Profile:

| time | substrate 5a | 9-decenol-9-decenoate 7 | dec-9-enol 6a | decanol 6b |
| --- | --- | --- | --- | --- |
| 0 h | 100% | 0% | 0% | 0% |
| 2 h | 17% | 18% | 65% | 0% |
| 3 h | 7% | 13% | 80% | 0% |
| 4 h | 1% | 4% | 93% | 3% |
| 5 h | 0% | 0% | 96% | 4% |

EXAMPLE 10

Undec-10-en-1-yl undec-10-enoate 3a was prepared as described by B. Kowalczyk et al., *Angew. Chem. Int. Ed.* 49, 5737, 2010.

The reaction is carried out as described in Example 9 using catalyst 4a (4.2 mg, 0.02%) in styrene (1.25 g, 12 mmol) and KOMe (180 mg, 2.5 mmol) in undec-10-en-1-yl undec-10-enoate 3a (8.4 g, 25 mmol). After 8 hours an 98% conversion to 90% undec-10-enol 2a and 8% undecanol 2b was detected by GC. CO/DB selectivity 92:8.

EXAMPLE 11

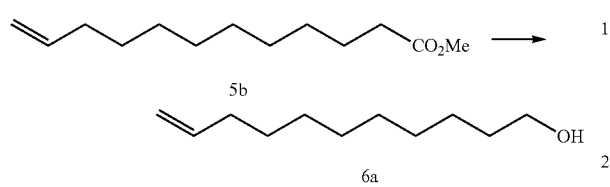

For the preparation of substrate 5b see for example S. P. Morcillo et al., *J. Org. Chem.* 76, 2277, 2011.

The reaction is carried out as described in Example 9 using catalyst 4a (4.5 mg, 0.01%) in styrene (2.5 g, 23 mmol) and KOMe (380 mg, 5.4 mmol) in methyl dec-9-enoate 5b (10 g, 54 mmol). After 7 hours a 94% conversion to 85% dec-9-enol 6a and 9% dec-9-en-1-yl dec-9-enoate 7 was detected by GC.

EXAMPLE 12

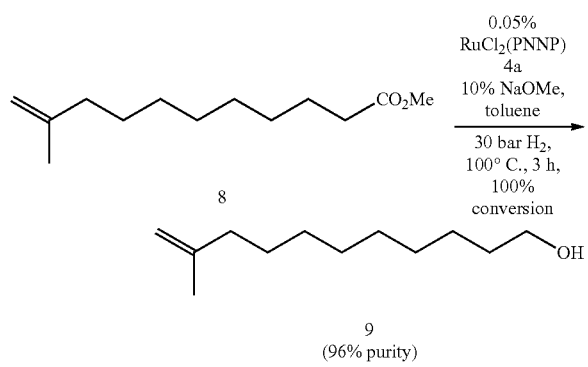

Under argon, toluene (2 ml) is added to a glass vial (10 ml) containing a magnetic stirring bar, RuCl$_2$(PNNP) 4a (1.7 mg, 0.05%) and NaOMe (23.0 mg, 10%). To this suspension methyl 10-methylundec-10-enoate 8 (0.9 g, 4.24 mmol) is added, prepared according to A. Sharma et al., *Tetrahedron Lett.* 48, 3705, 2007. The vial is capped (crimp cap & silicone septum), punctured with a needle and put in an autoclave. Whilst stirring the autoclave is flushed once with argon, twice with hydrogen, put under hydrogen pressure (30 bar) and heated to 100° C. After three hours the heating is stopped and the pressure released. An aliquot of the reaction mixture is taken and diluted with MTBE (1.5 ml) for GC-MS and NMR analyses which show 100% conversion of 8 to 10-methylundec-10-en-1-ol 9 (96%) and 10-methylundec-10-en-1-yl-10-methylundec-10-enoate 10 (4%).

Analytical Data of 9:

$^1$H-NMR (400 MHz, CDCl$_3$): 4.67 (d, J=9.35, 2H), 3.60 (t, J=6.70, 2H), 1.99 (t, J=7.58, 2H), 1.70 (s, 3H), 1.55 (m, 2H), 1.41 (m, 2H), 1.37-1.21 (m, 10H). $^{13}$C-NMR (400 MHz, CDCl$_3$): 146.23, 109.55, 62.74, 37.84, 32.73, 29.60, 29.49, 29.46, 29.32, 27.63, 25.78, 22.37. GC/MS: 184 (1%, M$^+$), 166 (2%, [M−18]$^+$), 151 (3%), 138 (2%), 123 (8%), 109 (16%), 95 (32%), 82 (54%), 69 (75%).

Analytical Data of 10-methylundec-10-en-1-yl-10-methylundec-10-enoate 10:

GC/MS: 364 (1%, M$^+$), 199 (2%), 181 (9%), 163 (5%), 150 (7%), 137 (10%), 123 (15%), 110 (24%), 95 (48%), 82 (55%).

EXAMPLE 13

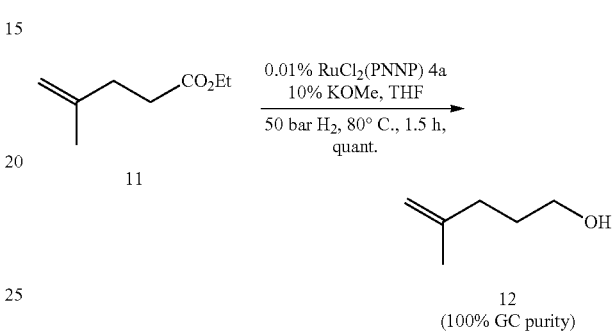

The reaction is carried out as described in Example 8 but using catalyst 4a (7.6 mg, 0.01%) in THF (5 ml) and KOMe (0.63 g, 9 mmol) in ethyl 4-methylpent-4-enoate 11 (12.9 g, 91 mmol) and THF (58 ml). Standard work-up gave a slightly yellow crude oil (5.6 g, 61%) which contained 4-methyl pent-4-en-1-ol 12 of 100% purity according to GC.

The analytical data of 4-methylpent-4-en-1-ol 12 were identical with the ones obtained from commercial samples of this compound.

The invention claimed is:

1. A process for the chemoselective reduction of a terminally unsaturated carboxylic ester (I) to a terminally unsaturated alcohol (II)

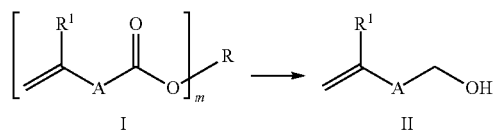

wherein A is a divalent radical containing 1 to 30 carbon atoms, which may be linear or branched, substituted or unsubstituted aliphatic, aromatic or contain both aliphatic and aromatic elements; R is a hydrocarbon radical or a radical derived from a hydrocarbon, which may be substituted or unsubstituted and saturated or unsaturated; R$_1$ is a hydrogen atom or a C$_{1-20}$ linear or branched, substituted or unsubstituted alkyl or alkene group; and m is an integer from 1 to 6, by catalytic hydrogenation in the presence of a ruthenium (II) complex, wherein the concentration of the ruthenium (II) complex is less than 0.05 mol %.

2. The process for the chemoselective reduction of a terminally unsaturated carboxylic ester to a terminally unsaturated alcohol by catalytic hydrogenation in the presence of the ruthenium (II) complex according to claim 1

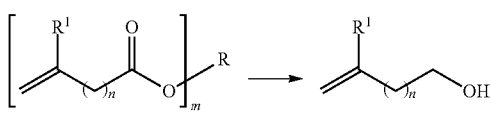

wherein R, $R_1$ and m are as defined, and wherein n is an integer from 1 to 10.

3. The process according to claim 1, wherein the terminally unsaturated carboxylic ester is selected from the group consisting of methyl 9-decenoate, ethyl 9-decenoate, methyl 10-undecenoate and ethyl 10-undecenoate.

4. The process according to claim 1 wherein the terminally unsaturated carboxylic ester (I) is represented by the formula

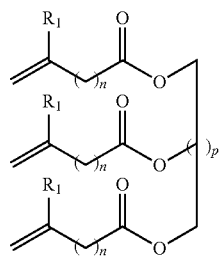

wherein p is zero or an integer from 1 to 4.

5. The process according to claim 1 wherein the conversion of the terminally unsaturated carboxylic ester is greater than 80%.

6. The process according to claim 1 wherein at greater than 80% conversion of the terminally unsaturated carboxylic ester the chemoselectivity is such that the ratio of unsaturated alcohol to saturated alcohol is 6:1 or greater, optionally 7:1 or greater, further optionally 8:1 or greater, further optionally 9:1, further optionally 10:1 or greater.

7. The process according to claim 1 wherein the ruthenium complex is a complex with a tetradentate ligand wherein the coordinating groups of said tetradentate ligand consist of at least one imino or amino group and at least one phosphino group.

8. The process according to claim 1 wherein the ruthenium complex is represented by the formula 4a or 4b

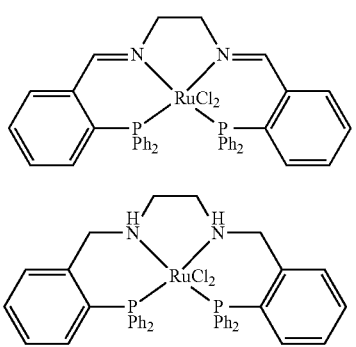

9. The process according to claim 1 wherein the molar ratio of terminally unsaturated carboxylic ester/ catalyst (substrate/catalyst ratio) is greater than 2000, optionally greater than 10000, further optionally greater than 20000.

10. The process according to claim 1 wherein the terminally unsaturated carboxylic ester is an ethyl ester or a higher ester, selected from n-propyl, iso-propyl, n-butyl, tert-butyl or iso-butyl ester.

11. The process according to claim 1 carried out in a solvent, employed at a level of less than 100% weight/weight (w/w) equivalents based on the amount of terminally unsaturated carboxylic ester, optionally less than 50% w/w, further optionally less than 25% w/w, further optionally less than 10% w/w.

12. The process according to claim 1 that is carried out in the absence of solvent.

13. The process according to claim 1 carried out in a basic medium.

14. The process according to claim 13 wherein the base is a metal alkanoate, wherein the metal may optionally be Na, K or Cs and the alkanoate is a $C_1$ to $C_{10}$ alkanoate, which may be linear or branched.

15. The process according to claim 13 wherein the base/ solvent mixture is NaOMe/ toluene or KOMe/THF.

16. A process for the chemoselective reduction of a terminally unsaturated carboxylic ester (I) to a terminally unsaturated alcohol (II) by catalytic hydrogenation, optionally in the presence of a transition metal complex, further optionally in the presence of a ruthenium (II) complex

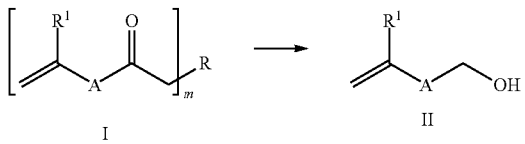

wherein A is a divalent radical containing 1 to 30 carbon atoms, which may be linear or branched, substituted or unsubstituted aliphatic, aromatic or contain both aliphatic and aromatic elements; R is a hydrocarbon radical or a radical derived from a hydrocarbon, which may be substituted or unsubstituted and saturated or unsaturated; $R_1$ is a hydrogen atom or a $C_{1-20}$ linear or branched, substituted or unsubstituted alkyl or alkene group; and m is an integer from 1 to 6, and wherein a sacrificial alkene V is added to the reaction mixture

selected from the group consisting of terminal monosubstituted alkenes wherein R'=H, and 1,1-disubstituted methylene compounds wherein R and R'≠H.

17. The process according to claim 16 in which the sacrificial alkene is added in amounts of 0.1-10 mol-equivalents.

18. The process according to claim 16 in which the sacrificial alkene is selected from the group of substituted styrenes or styrene.

19. A method of forming 9-decenol by the chemoselective reduction of the carboxylic ester methyl 9-decenoate or ethyl 9-decenoate according to the process as defined in claim 3.

20. A method of forming 9-decenol by the chemoselective reduction of the carboxylic ester methyl 9-decenoate or ethyl 9-decenoate according to the process as defined in claim 16.

* * * * *